United States Patent [19]

Gallagher et al.

[11] Patent Number: 4,892,963
[45] Date of Patent: Jan. 9, 1990

[54] N-PHENYL AMIDE COMPOUNDS

[75] Inventors: Peter T. Gallagher, Camberley; Terence A. Hicks, Fleet; Graham W. Mullier, Aldershot, all of Great Britain

[73] Assignee: Lilly Industries Limited, Basingstoke, England

[21] Appl. No.: 83,538

[22] Filed: Aug. 7, 1987

[30] Foreign Application Priority Data

Aug. 8, 1986 [GB] United Kingdom ............... 8619432

[51] Int. Cl.$^4$ ............... A61K 31/165; A61K 31/42; A61K 31/275
[52] U.S. Cl. ............... 558/414; 558/423; 514/885; 514/908
[58] Field of Search ............... 558/414, 303, 388, 401, 558/411, 418, 423, 425, 432; 564/123, 161, 162, 163, 189, 192, 193, 201, 209, 215; 514/183, 359, 378, 449, 461, 613, 740, 741, 885, 908

[56] References Cited

U.S. PATENT DOCUMENTS 4,061,767 12/1977 Ertel et al. ............... 424/282

FOREIGN PATENT DOCUMENTS 2654797 6/1978 Fed. Rep. of Germany .
1571990 7/1980 United Kingdom .
1596383 8/1981 United Kingdom .

Primary Examiner—William R. Dixon, Jr.
Assistant Examiner—James M. Hunter, Jr.
Attorney, Agent, or Firm—Paul C. Steinhardt; Robert A. Conrad; Leroy Whitaker

[57] ABSTRACT

Compounds of the following formula have pharmaceutical properties:

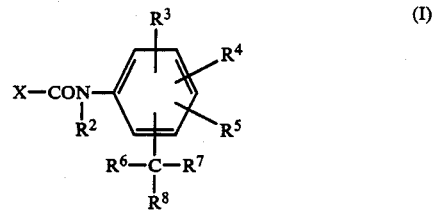

in which X is $R^1(HO)C=C(CN)—$, $R^1(CO)—CH(CN)—$ or

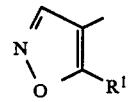

$R^1$ and $R^2$ are each hydrogen or $C_{1-6}$ alkyl, $R^3$, $R^4$ and $R^5$ are each hydrogen, hydroxy, halogen, nitro, cyano, carboxy, $C_{1-4}$ alkyl, $C_{1-4}$ alkoxy, $C_{1-4}$ alkylthio, halo-substituted $C_{1-4}$ alkyl, halo-substituted $C_{1-4}$ alkoxy, halo-substituted $C_{1-4}$ alkylthio, $C_{2-5}$ alkoxycarbonyl, optionally substituted phenyl, optionally substituted phenoxy, $R'R''N-$ where $R'$ and $R''$ are each hydrogen or $C_{1-4}$ alkyl $R'''CONH-$ where $R'''$ is $C_{1-4}$ alkyl, $R^6$, $R^7$ and $R^8$ are each $C_{1-6}$ alkyl, halo-substituted $C_{1-6}$ alkyl or optionally substituted phenyl, or $R^6$ and $R^7$, together with the carbon atom to which they are attached, form a cycloalkyl group containing 3 to 7 carbon atoms, or $R^6$, $R^7$ and $R^8$ together with the carbon atom to which they are attached, form a bicycloalkyl group containing 4 to 9 carbon atoms; and salts thereof.

9 Claims, No Drawings

N-PHENYL AMIDE COMPOUNDS

This invention relates to novel compounds and their use as pharmaceuticals.

Certain phenyl butenamide compounds with pharmaceutical properties are disclosed in British Patent 1 571 990. The compounds are optionally substituted with various substituents on the phenyl nucleus including methyl or ethyl.

The compounds of the invention are of related structure but require the presence of a substituent attached to the phenyl ring by a tertiary carbon atom which confers optimum biological activity on the molecule.

The compounds of the invention have the following general formula

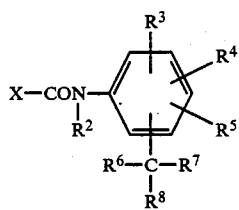

(I)

in which X is $R^1(HO)C=C(CN)-$, $R^1(CO)-CH(CN)-$ or

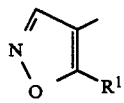

$R^1$ and $R^2$ are each hydrogen or $C_{1-6}$ alkyl, $R^3$, $R^4$ and $R^5$ are each hydrogen, hydroxy, halogen, nitro, cyano, carboxy, $C_{1-4}$ alkyl, $C_{1-4}$ alkoxy, $C_{1-4}$ alkylthio, halo-substituted $C_{1-4}$ alkyl, halo-substituted $C_{1-4}$ alkoxy, halo-substituted $C_{1-4}$ alkylthio, $C_{2-5}$ alkoxycarbonyl, optionally substituted phenyl, optionally substituted phenoxy, R'R''N— where R' and R'' are each hydrogen or $C_{1-4}$ alkyl or R'''CONH— where R''' is $C_{1-4}$ alkyl, $R^6$, $R^7$ and $R^8$ are each $C_{1-6}$ alkyl, halo-substituted $C_{1-6}$ alkyl or optionally substituted phenyl, or $R^6$ and $R^7$, together with the carbon atom to which they are attached, form a cycloalkyl group containing 3 to 7 carbon atoms, or $R^6$, $R^7$ and $R^8$ together with the carbon atom to which they are attached, form a bicycloalkyl group containing 4 to 9 carbon atoms; and salts thereof.

The compounds of the invention and their pharmaceutically-acceptable salts are active in tests which show their potential for treating immune diseases such as arthritis, and for treating diseases in which leukotrienes are implicated.

It will be appreciated that compounds of the formula (I) above, in which X is $R^1(HO)C=C(CN)-$, can exist in tautomeric and isomeric form as indicated by the following equilibria:

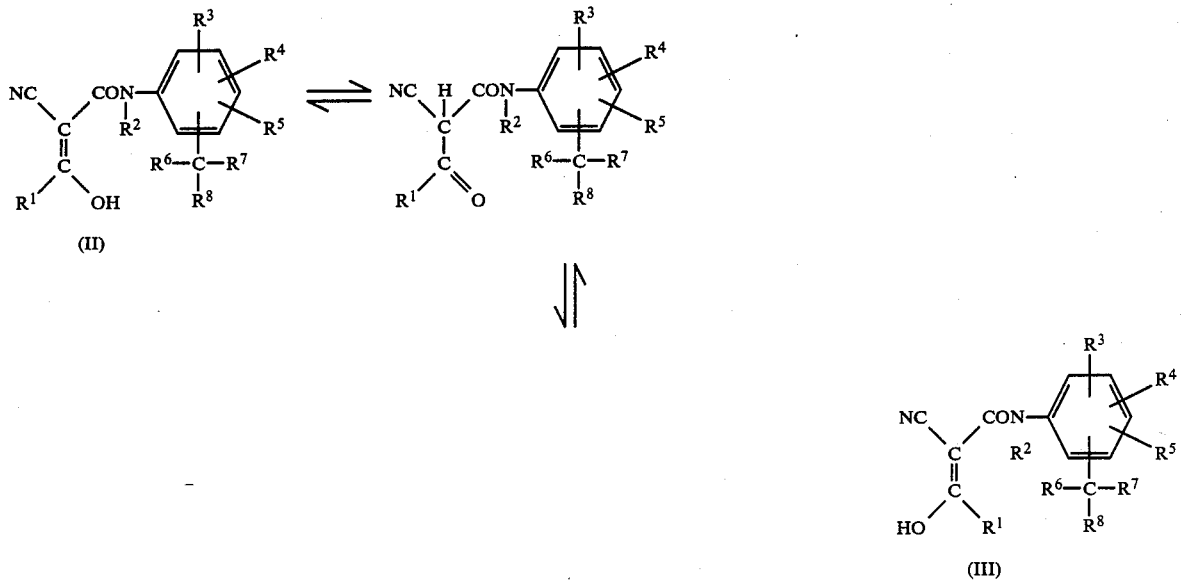

When prepared by the usual methods of synthesis the compounds are a mixture of the Z and E isomers, (II) and (III) above, in which the Z form predominates. The Z and E forms can be separated by conventional crystallisation techniques. The keto form is an intermediate in the synthesis of the isomers (II) and (III).

In formula (I) a $C_{1-6}$ alkyl group can be branched or unbranched and can be, for example, methyl, ethyl, propyl, 1-methylethyl, butyl, 1-methylpropyl, 1,1-dimethylethyl, pentyl or hexyl. Similarly a $C_{1-4}$ alkyl can be methyl, ethyl, propyl or 1-methylethyl, and $C_{1-4}$ alkoxy and $C_{1-4}$ alkylthio are derived from such groups being attached to the phenyl ring by an oxygen or sulphur atom, respectively. When such groups are halo-substituted one or more of the hydrogen atoms is replaced by a halo atom, which is preferably fluoro, chloro or bromo and especially fluoro or chloro. A preferred example of halo-substituted alkyl is the trifluoromethyl substituent. $R^3$, $R^4$ and $R^5$ can also be halogen and is preferably fluoro, chloro or bromo. When $R^3$, $R^4$ or $R^5$ is a $C_{2-5}$ alkoxycarbonyl group it is of the formula ROCO— where R is a $C_{1-4}$ alkyl group, and when $R^3$, $R^4$ or $R^5$ is optionally substituted phenyl or optionally substituted phenoxy, it is preferred that the phenyl group is optionally substituted with 1 to 3 groups selected from, halogen, nitro, cyano, carboxy, $C_{1-4}$ alkyl, $C_{1-4}$ alkoxy, $C_{1-4}$ alkylthio, halo-substituted $C_{1-4}$ alkyl, halo-substituted $C_{1-4}$ alkoxy, halo-substituted $C_{1-4}$ alkylthio and $C_{2-5}$ alkoxycarbonyl.

When $R^6$ and $R^7$ form a cycloalkyl group, the cycloalkyl group can be cyclopropyl, cyclobutyl, cyclopentyl, cyclohexyl or cycloheptyl, and when $R^6$, $R^7$ and $R^8$ together form a bicyclo radical the radical preferably contains 4 to 7 carbon atoms, an example being bicyclo [4.1.0] heptyl.

It is, of course, possible to prepare salts of the compounds of the invention because of the presence of the acidic hydroxyl group. Such salts are included in the invention. They can be any of the well known base addition salts. Examples of such salts are those derived from ammonium hydroxide and alkali and alkaline earth metal hydroxides, carbonates and bicarbonates, as well as salts derived from aliphatic and aromatic amines, aliphatic diamines and hydroxy alkylamines. Bases especially useful in the preparation of such salts include ammonium hydroxide, potassium carbonate, sodium bicarbonate, calcium hydroxide, methylamine, diethylamine, ethylene diamine, cyclohexylamine and ethanolamine. The potassium and sodium salt forms are particularly preferred. Ther may in addition be the salt-forming groups on the phenyl ring, providing both base and acid addition salts. It is preferred that the salt is pharmaceutically-acceptable but other salts are included in the invention since they may be used in the preparation of other compounds or to obtain good crystalline forms.

Preferred compounds of formula (I) are those in which:

(i) X is $R^1$ (HO)C=C(CN)— and more specifically

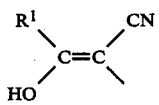

(ii) $R^4$ and $R^5$ are hydrogen
(iii) $R^3$, $R^4$ and $R^5$ are hydrogen
(iv) $R^2$ is hydrogen
(v) $R^2$ is methyl
(vi) $R^1$ is $C_{1-6}$ alkyl, preferably methyl
(vii) $R^6$, $R^7$ and $R^8$ are each $C_{1-6}$ alkyl
(viii) $R^6$ and $R^7$ together form a cycloalkyl group of 3 to 7 carbon atoms and $R^8$ is $C_{1-6}$ alkyl
(ix) the —$CR^6R^7R^8$ group is attached to the phenyl ring at the para position, with respect to the amido group.

A preferred group of compounds is of the formula

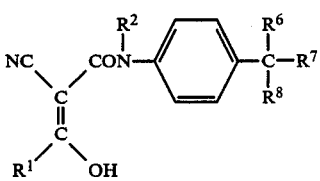

in which $R^1$ is $C_{1-4}$ alkyl, $R^2$ is hydrogen or methyl, and $R^6$, $R^7$ and $R^8$ are each $C_{1-4}$ alkyl; and salts thereof.

A further preferred group of compounds is of the formula

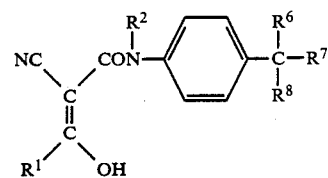

in which $R^1$ is $C_{1-4}$ alkyl, $R^2$ is hydrogen or methyl, $R^6$ and $R^7$ together form a cycloalkyl group of 3 to 7 carbon atoms and $R^8$ is $C_{1-6}$ alkyl, and salts thereof.

The invention also comprises a process for producing compounds of formula (I) which comprises (a) reacting a compound of the formula

in which M is a monobasic metal ion, with a compound of the formula

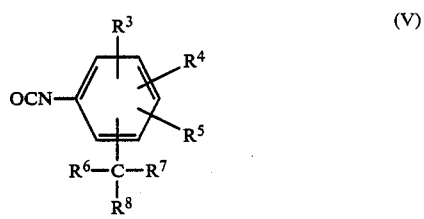

where $R^1$ and $R^3$ to $R^8$ have the values given above, and optionally reacting the salt thus formed with acid to liberate the free hydroxyl compound in which X is $R^1$(HO)C=C(CN)—, (b) reacting a compound of the formula

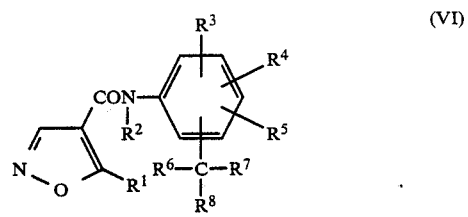

where $R^1$ to $R^8$ have the values given above, with base, and optionally reacting the salt thus formed with acid to liberate the free hydroxyl compound in which X is $R^1$(HO)C=C(CN)—, (c) reacting a compound of the formula

with an amine of the formula

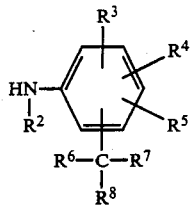

(VIII)

where Y is halo, preferably chloro, to give a compound in which X is

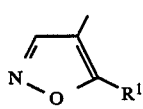

or (d) hydrolysing a compound of the formula

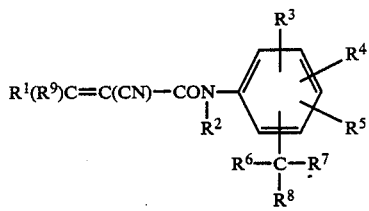

(IX)

where $R^1$ to $R^8$ have the values given above and $R^9$ is a leaving group.

The reaction (a) referred to above is preferably carried out in an inert organic solvent such as for example tetrahydrofuran and at a temperature of from $-30°$ C. to $100°$ C., yielding a salt of the formula

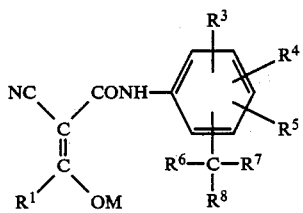

which can be converted to the free hydroxyl compound shown in formula (I) by action of acid such as aqueous mineral acid, for example hydrochloric acid, at a temperature of from $0°$ C. to $100°$ C.

Compounds of formula (IV) can be prepared by ring opening the appropriate isoxazole derivative of formula

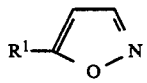

by the action of base such as, for example, alkali metal alkoxide in ethanol at a temperature of for example $5°$ C. to $80°$ C. to give a compound in which M is an alkali metal ion, or by reacting 5-methylisoxazole with butyl lithium in tetrahydrofuran at a temperature of from $-80°$ C. to $30°$ C. to give a compound in which M is lithium, optionally followed by reaction with the appropriate alkyl bromide or iodide to give reactants of formula (IV) in which $R^1$ is $C_{2-6}$ alkyl. Compounds of formula (V) are either commercially available or can be synthesised by conventional methods such as by reacting the appropriate benzoic acid derivative with diphenyl phosphoryl azide and triethylamine in dimethylformamide and heating the azide thus produced under reflux.

With regard to reaction (b), this reaction is preferably performed in an inert organic solvent such as for example tetrahydrofuran, ethanol or dimethylsulphoxide, at a temperature of from $-80°$ C. to $100°$ C.

Reactants of formula (VI) can be readily prepared by condensing an isoxazolyl halide of the formula

(VII)

where Z is halo preferably chloro, with an appropriate amine of the formula

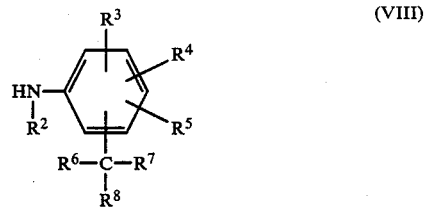

(VIII)

The reaction is preferably carried out at a temperature of from $-70°$ C. to $110°$ C. in an inert organic solvent such as for example toluene.

Compounds of formula (VII) can be prepared by a sequence of reactions, for example, as follows

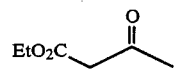

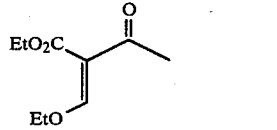

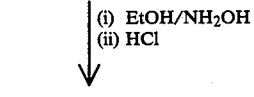

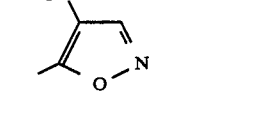

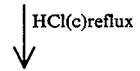

-continued

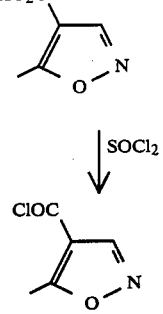

Compounds of formula (VIII) in which $R^2$ is $C_{1-6}$ alkyl can be prepared from the corresponding aniline by a suitable technique of alkylation, for example, by treatment with formyl acetic anhydride followed by reduction with lithium aluminium hydride to give the compound in which $R^2$ is methyl, or by acylation with the appropriate alkenoyl halide followed by reduction with lithium aluminium hydride to give compounds in which $R^2$ is $C_{2-6}$ alkyl. Alternatively the compounds can be prepared by reducing the corresponding isocyanate employing, for example, lithium aluminium hydride in ether.

When $R^6$, $R^7$ or $R^8$ comprise cyclic groups special methods are required for the preparation of the starting materials, though all the steps involved are conventional reaction steps. For example the following synthetic scheme shows a route for preparing a typical reactant.

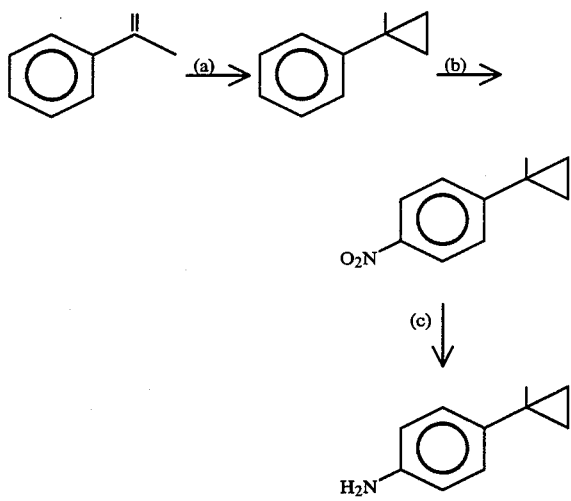

(a) Simmonds Smith reaction
(b) reaction of nitric acid, acetic acid and acetic anhydride at 5° C.
(c) stannous chloride in ethyl acetate The reaction (d), referred to above, is preferably carried out in aqueous medium at a temperature of from 5° C. to 100° C. Mineral acid such as hydrochloric acid or alkali metal base for example sodium hydroxide can be employed. $R^9$ is a leaving group that is removed in the hydrolysis reaction and is especially $C_{1-4}$ alkoxy, phenoxy or R'R"N— where R' and R" re each $C_{1-4}$ alkyl.

Compounds of formula (IX) can be prepared from the appropriate amine of formula

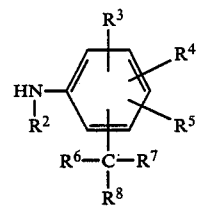

by reaction firstly with cyanoacetic acid or an ester of cyanoacetic acid, a reaction which proceeds by use of a dehydrating agent for example dicyclohexyl carbodiimide in a suitable solvent such as dichloromethane, or by the application of heat, to give a compound of formula

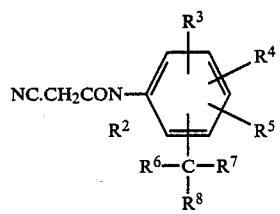

which on reaction with trialkylorthoacetate or higher alkanoate, in acetic anhydride and preferably with a catalytic amount of a Lewis acid such as zinc chloride, gives the desired intermediate.

It will be appreciated that the substituents on the phenyl ring shown in formula (I) can be interchanged. For instance a carboxyl substituent on the ring or a carboxyl attached to a phenyl substituent on the ring can be prepared by hydrolysis of the appropriate nitrile or alkoxycarbonyl derivative, after the main condensation reaction step has been performed.

The compounds of the invention have been shown to modify the immune response in tests which establish that they inhibit concanavalin A-induced T-cell proliferation and graft versus host reaction, a T-cell mediated process. The compounds are also active in the adjuvant arthritis test (B. B. Newbould Chemotherapy of Arthritis Induced in Rats by Mycobacterial Adjuvant, Br. J. Pharmacol. 21, 127–136 (1963)).

These properties show that the compounds of the invention have anti-inflammatory properties and are indicated for use in the treatment of, for example, arthritis, and also immune diseases such as systemic lupus and graft rejection.

Preferred compounds, such as for example 2-cyano-N-[4-(1,1-dimethylethyl)phenyl]-3-hydroxybut-2-enamide and 2-cyano-N-[4-(1,1-dimethylethyl)phenyl]-3-hydroxy-N-methylbut-2-enamide, exhibit little or no cyclooxygenase inhibiting properties as shown in the test described by J. Harvey and D. J. Osborn, J. Pharmacological Methods 9, 147–155 (1983), and in this respect differ from conventional anti-inflammatory agents. Other members of the series inhibit 5-lipoxygenase product formation as measured in this test, and are thus indicated for the therapeutic treatment of diseases in which leukotrienes are implicated. These include immediate hypersensitivity diseases, allergic reactions of the pulmonary system, for example, in lung disorders such as extrinsic asthma and industrial asthmas and in other inflammatory disorders associated with acute or chronic infectious diseases as allergic skin diseases, ectopic and atopic eczemas, psoriasis, contact hypersensitivity and angioneurotic oedema, bronchitis, cystic fibrosis and rheumatic fever. Furthermore, owing to their inhibition of leukotriene formation, the compounds have potential activity against a wide range of inflammatory diseases, and are also indicated for use in cancer treatment.

The compounds may be administered by various routes, for example, by the oral or rectal route, by inhalation, topically or parenterally, for example by injection, being usually employed in the form of a pharmaceutical composition. Such compositions form part of the present invention and are prepared in a manner well known in the pharmaceutical art and normally comprise at least one active compound in association with a pharmaceutically acceptable diluent or carrier. In making the compositions of the present invention, the active ingredient will usually be mixed with a carrier, or diluted by a carrier, and/or enclosed with a carrier which may, for example, be in the form of a capsule, sachet, paper or other container. There the carrier serves as a diluent, it may be solid, semi-solid, or liquid material which acts as a vehicle, excipient or medium for the active ingredient. Thus, the composition may be in the form of tablets, lozenges, sachets, cachets, elixirs, suspensions, aerosols, as a solid or in a liquid medium, ointments containing, for example, up to 10% by weight of the active compound, soft and hard gelatin capsules, suppositories, injection solutions and suspensions and sterile packaged powders. For administration by inhalation, particular forms of presentation include aerosols, atomisers and vaporisers.

Some examples of suitable carriers are lactose, dextrose, sucrose, sorbitol, mannitol, starch, gum acacia, calcium phosphate, alginates, tragacanth, gelatin, syrup, methyl cellulose, methyl- and propyl-hydroxybenzoate, talc, magnesium stearate and mineral oil. The compositions of the invention may, as is well known in the art, be formulated so as to provide quick, sustained or delayed release of the active ingredient after administration to the patient.

Where the compositions are formulated in unit dosage form, it is preferred that each unit dosage form contains from 5 mg to 500 mg, more usually 25 to 200 mg, of the active ingredient. The term "unit dosage form" refers to physically discrete units suitable as unit dosage for human subjects and animals, each unit containing a predetermined quantity of active material calculated to produce the desired therapeutic effect, in association with the required pharmaceutical carrier.

The compounds are effective over a wide dosage range and for example dosages per day will normally fall within the range of 0.5 to 300 mg/kg and in the treatment of adult humans, more usually in the range of from 5 to 100 mg/kg. However, it will be understood that the amount of the compound actually administered will be determined by a physician, in the light of the relevant circumstances including the condition to be treated, the choice of compound to be administered and the chosen route of administration and therefore the above dosage ranges are not intended to limit the scope of the invention in any way.

The following Examples illustrate the invention. The compounds of formula (I) in which X is $R^1(HO)C=C(CN)—$ are prepared initially as a mixture of Z and E isomers in which the Z form predominates.

On purification the pure Z isomer was obtained as the product.

EXAMPLE 1

(i) Cyanoacetone Sodium salt

Sodium lumps (7.36 g) were allowed to dissolve, with mechanical stirring, in absolute ethanol (368 ml), the reaction being carried out under nitrogen. The resulting hot solution was stirred until the temperature fell to about 20° C.

5-Methylisoxazole (26.56 g) was added dropwise during 12 minutes. The resulting hot white suspension was stirred for 1 hour 12 minutes, then cooled in an ice-bath and stirred for 1 hour 24 minutes.

The white solid was removed by filtration, and washed on the filter with 40–60 petroleum ether (50 ml). It was dried in vacuo in the oven at 46° C. to give cyanoacetone, sodium salt.

(ii) 2-Cyano-N-[4-(1,1-dimethylethyl)phenyl]-3-hydroxybut-2-enamide

Cyanoacetone, sodium salt (4.88 g), was magnetically stirred under nitrogen, in freshly sodium dried and distilled tetrahydrofuran (70 ml).

A solution of 4-(1,1-dimethylethyl)-phenylisocyanate (8.06 g) in dry tetrahydrofuran (38 ml) was added, with ice-bath cooling, during 7 minutes at 1.5° C. to 5° C. The resulting suspension was stirred for a further 10 minutes, with the ice-bath removed, then at 66° C. in an oil-bath for 30 minutes.

The resulting slightly turbid yellow solution was evaporated at 50° C. in vacuo (water pump) to leave a cream coloured foam.

Ice/water (100 ml) and methanol (16 ml) were added, stirred, and adjusted to pH 1 by addition of concentrated HCl. The white solid was filtered off and washed on the filter (×2) with a mixture of absolute ethanol (20 ml) and water (20 ml). The solid was dried at 50° C. in vacuo in the oven, then dissolved in boiling absolute ethanol (190 ml), with magnetic stirring. The heating mantle was removed and stirring continued, for 4 hours at ambient temperature. The white crystalline solid was filtered off and dried at 56° C. in vacuo in the oven to give the title compound, 2-Cyano-N-[4-(1,1-dimethylethyl)phenyl]-3-hydroxybut-2-enamide (m.p. 134°–135° C.).

EXAMPLE 2

(i) Ethyl ethoxymethyleneacetoacetate

Ethyl acetoacetate (130.14 g), triethylorthoformate (148.2 g) and acetic anhydride (204.18 g) were heated under reflux for 90 minutes. The more volatile by-products were removed on a rotary evaporator, leaving a dark red oil (approximately 400 ml). This was distilled at reduced pressure through a 15 cm Vigreaux column, giving 128 g of a clear oil (b.p. 100°–110° C., 1 mm Hg). The product was a 1:1 mixture of Z and E ethyl ethoxymethyleneacetoacetate.

(ii) Ethyl 5-methylisoxazol-4-yl carboxylate

Hydroxylamine hydrochloride (52.6 g) was dissolved in water (150 ml) and stirred while an ice-cold solution of sodium hydroxide (30.28 g) in water (100 ml) was added. This solution was stirred for 15 minutes then absolute ethanol (600 ml) added and the solution stirred for a further 15 minutes. Ethyl ethoxymethyleneacetoacetate (128 g) was dissolved in absolute ethanol (100 ml) and added to the hydroxylamine solution. After stirring for 30 hours the solvents were removed on a rotary evaporator (bath at 45° C.). The clear oil was distilled at reduced pressure through a 15 cm Vigreaux column. Product collected as a clear oil at 50°–54° C./0.5 mm Hg.

(iii) 5-Methylisoxazol-4-yl carboxylic acid

Ethyl 5-methylisoxazol-4-yl carboxylate (65 g) was heated under reflux in 10M HCl (500 ml) for 3 hours. On cooling the product crystallised out. This was filtered and dried giving 42 g of a white crystalline solid, m.p. 134°–136° C.

(iv) 5-Methylisoxazol-4-yl carbonyl chloride

Thionyl chloride (118 g) was added to 5-methylisoxazol-4-yl carboxylic acid (42 g) and stirred at room temperature as dimethylformamide (0.2 ml) was added. The solution was heated under reflux for 2 hours with stirring. Excess thionyl chloride was removed in vacuo at 50° C., then the residue was distilled through a 15 cm Vigreaux column at reduced pressure to give an oil, b.p. 32°–34° C./0.1 mm Hg.

(v) 4-(1,1-Dimethylethyl)-N-methylbenzenamine

Lithium aluminium hydride (6.91 g) was added, under nitrogen, to magnetically stirred 3 A molecular sieve dried ether (200 ml) in over dried apparatus.

After cooling in an ice-bath, a solution of 1-(1,1-dimethylethyl)-4-isocyanatobenzene (15.98 g) supplied by EMKACHEMIE, in dry ether (10 ml) was added, dropwise during 57 minutes at 3° C. to 10° C.

The ice-bath was removed and after 8 minutes stirring the reaction mixture was heated under reflux for 1 hour 17 minutes.

After cooling in an ice-bath, water (6.9 ml) was dropped in over 9 minutes, followed by 15% w/v aqueous sodium hydroxide (6.9 ml) during 23 minutes, then water (21 ml) over 48 minutes.

The resulting white suspension was allowed to stand at room temperature overnight. The white granular solid was removed by filtration and washed on the filter with ether.

The combined filtrate and washings were dried over MgSO4, filtered and evaporated in vacuo to leave a yellow oil/solid mixture.

The mixture was stirred in 40° C.–60° C. petroleum ether (15 ml) filtered and the white crystalline solid on the filter was washed with 40° C.–60° C. petroleum ether (2×15 ml).

The petroleum ether filtrate and washings were combined and evaporated in vacuo to leave a yellow oil.

Twice distilling the oil via a short Vigreaux column yielded two fractions, b.p. 76° C.–77° C./3.5 mm and b.p. 87° C.–88° C./3.5 mm which were combined and used in the next stage.

(vi) N-[4-(1,1-Dimethylethyl)phenyl]-N-methyl-5-methylisoxazol-4-ylcarboxamide A solution of 5-methylisoxazol-4-yl carbonyl chloride (6.51 g) in type 3 A molecular sieve dried dichloromethane (7 ml) was added dropwise to an ice-bath cooled, magnetically stirred solution of 4-(1,1-dimethylethyl)-N-methylbenzenamine (7.3 g) and 3 A mole sieve dried pyridine (3.96 g) in dry dichloromethane (40 ml).

The addition was made over 23 minutes at 3.5° C. to 17° C. During this time a crystalline solid separated.

The cooling-bath was removed and stirring was continued for 25.5 hours at ambient temperature.

The reaction mixture was poured into water (100 ml) and, after shaking, the upper aqueous phase was removed and extracted with dichloromethane (50 ml).

The dichloromethane solutions were combined and washed with 1.5 N hydrochloric acid (75 ml), than water (3×75 ml). After drying over MgSO4 and filtering, evaporation in vacuo, a buff-coloured product remained, (m.p. 100° C.).

(vii) 2-Cyano-N-[4-(1,1-dimethylethyl)phenyl]-3-hydroxy-N-methylbut-2-enamide N-[4-(1,1-Dimethylethyl)phenyl]-N-methyl-5-methylisoxazol-4-ylcarboxamide (9.8 g) was magnetically stirred in absolute ethanol (200 ml) and 1N potassium hydroxide solution (36 ml). Within 10 minutes a clear solution had resulted.

After stirring for 26 hours at ambient temperature the solution was evaporated at 45° C. in vacuo to leave a light brown liquid, which was shaken in water (200 ml) and ether (100 ml).

The aqueous phase (pH 8) was removed, washed again with ether (100 ml) then adjusted to pH 1 by addition of 5N hydrochloric acid.

The cream coloured precipitate was removed by filtration and washed on filter with water (total volume 700 ml).

After drying at 45° C. in vacuo a solid product was obtained, m.p. 110° C.

Recrystallisation from 83% aqueous ethanol yielded crystals of pure product, m.p. 111°–112° C.

EXAMPLE 3

(i) 4-(1,1-Dimethylethyl)benzenamine

Absolute ethanol (20 ml) was added to 10% palladium on charcoal (0.2 g) in a Parr hydrogenation bottle (500 ml volume). 1-(1,1-Dimethylethyl)-4-nitrobenzene (50 g) in absolute ethanol (100 ml) was added. Hydrogen was admitted to the bottle and the mixture shaken at 60 psi over night. The catalyst was removed by filtration through Celite under nitrogen, the filtrate was reduced in vacuo and the residue distilled at 96° C./0.3 mm Hg to give 4-(1,1-dimethylethyl)benzenamine as an oil.

(ii) N-[4-(1,1-Dimethylethyl)phenyl]-5-methylisoxazol-4-yl-carboxamide

To a stirred solution of 4-(1,1-Dimethylethyl)benzenamine (2 g) and pyridine (1.06 g) in dry CHCl3 (50 ml) was added 5-methylisoxazol-4-ylcarbonyl chloride (1.95 g) in dry CHCl3 (10 ml) dropwise over 5 minutes under nitrogen at room temperature. After 20 hours the reaction mixture was washed with 2M HCl (2×100 ml) and brine (1×100 ml), dried over magnesium sulphate, and the solvent removed in vacuo. The product was recrystallised from 1:1 n-hexane:diethylether, m.p. 127° C.–128° C.

The following compounds were prepared similarly.
N-[2-Bromo-4-(1,1-dimethylethyl)phenyl]-5-methylisoxazol-4-yl-carboxamide, m.p. 134° C.–139° C. (from 1-amino-2-bromo-(1,1-dimethylethyl)benzene, b.p. 100/0.1 mm Hg).

N-[2-Chloro-4-(1,1-dimethylethyl)phenyl]-5-methylisoxazol-4-yl-carboxamide, m.p. 126° C.-127° C. (from 1-amino-2-chloro-(1,1-dimethylethyl)benzene, b.p. 84° C./0.1 mm Hg).

N-[4-(1,1-Dimethylpropyl)phenyl]-5-methylisoxazol-4-yl-carboxamide, m.p. 118° C.-120° C. (from 1-amino-4-(1,1-dimethylpropyl)benzene, JCS 1958, 2060-2062)

N-[4-(1,1-dimethylbutyl)phenyl]-5-methylisoxazol-4-carboxamide, viscous oil (from 1-amino-4-(1,1-dimethylbutyl)benzene, JACS 58, 439-441 (1936)).

N-[4-(1,1-dimethylpentyl)phenyl]-5-methylisoxazol-4-yl-carboxamide, viscous oil (from 1-amino-4-(1,1-dimethylpentyl)benzene, JACS 59, 2001-2003 (1937)).

N-[4-(1-methylcyclopropyl)phenyl]-5-methylisoxazol-4-yl-carboxamide, viscous oil (from 1-amino-4-(1-methylcyclopropyl)benzene, b.p. 65°-70° C./0.25 mm Hg, prepared by reduction of 1-(1-methylcyclopropyl)-4-nitrobenzene, Chem.Ber. 106 525-548 (1973)).

EXAMPLE 4

2-Cyano-N-[4-(1,1-dimethylpropyl)phenyl]-3-hydroxybut-2-enamide

N-[4-(1,1-dimethylpropyl)phenyl]-5-methylisoxazol-4-yl-carboxamide (2.612 g) was dissolved in absolute ethanol (150 ml) and stirred at room temperature as a solution of sodium hydroxide (0.383 g) in water (40 ml) was added dropwise. The reaction mixture was stirred for a further 16 hours at room temperature, then the ethanol was removed on a rotary evaporator (bath at 50° C.). The resulting aqueous solution was acidified with 2M HCl(aq) to pH 1. The white precipitate was collected by filtration, washed with water (4 ml) and dried in a vacuum oven at 50° C. The product had a melting point of 137°-138.5° C.

The following compounds were prepared similarly.

2-Cyano-N-[4-(1,1-dimethylbutyl)phenyl]-3-hydroxybut-2-enamide, m.p. 98°-100° C.

2-Cyano-N-[4-(1,1-dimethylpentyl)phenyl]-3-hydroxybut-2-enamide, m.p. 118°-119° C. (softens at 117° C.).

2-Cyano-N-[4-(1-methylcyclopropyl)phenyl]-3-hydroxybut-2-enamide, m.p. 159.5°-161° C. decomposed (softens at 157° C.).

EXAMPLE 5

The following pharmaceutical formulations are given by way of example (i) Injection formulation An injection formulation containing 5 mg/ml of active ingredient is prepared from the following

| Active ingredient | 250 mg |
|---|---|
| 0.1 M Sodium hydroxide | 10 ml |
| N/10 Hydrochloric acid | 2 ml |
| 5% Poloxamer F68 in isotonic saline to | 50 ml |

(ii) Hard gelatin capsule formulation

| Active ingredient | 100 mg |
|---|---|
| 1% Silicone starch | 50 mg |
| Starch flowable | 50 mg |

(iii) Tablet formulations

| Active ingredient | 100 mg |
|---|---|
| Microcrystalline cellulose | 185 mg |
| Carboxymethyl cellulose sodium (crosslinked) | 3 mg |
| Povidone | 10 mg |
| Magnesium stearate | 1 mg |

EXAMPLE 6

The concanavalin A response of rat spleen cells was used as a primary in vitro assay to determine the activity of the compounds of the invention. Many methods for the determination of concanavalin A response are described in the literature. The method employed was similar to that described by Lacombe P. et al, FEBS 3048 191, 227-230. This method was altered insofar as Hepes was excluded, $2 \times 10^5$ cells were used per culture well, and concanavalin A employed at 3 μg/ml. 2-Mercaptoethanol was a requirement ($2 \times 10_M{}^{-5}$) and 0.1 μCi of tritiated thymidine was added 4 hours before cell harvesting.

The compounds of the invention described in Examples 1, 3 and 4 all exhibited a greater than 50% inhibition at a dosage level of 10 micromolar.

We claim:

1. A compound of the formula

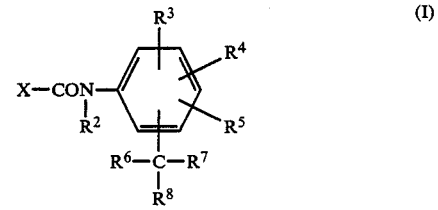

in which X is $R^1(HO)C=C(CN)—$, $R^1(CO)—CH(CN)—$ or

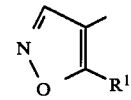

$R^1$ and $R^2$ are each hydrogen or $C_{1-6}$ alkyl, $R^3$, $R^4$ and $R^5$ are each hydrogen, hydroxy, halogen, nitro, cyano, carboxy, $C_{1-4}$ alkyl, $C_{1-4}$ alkoxy, $C_{1-4}$ alkylthio, halo-substituted $C_{1-4}$ alkyl, halo-substituted $C_{1-4}$ alkoxy, halo-substituted $C_{1-4}$ alkylthio, $C_{2-5}$ alkoxycarbonyl, phenyl, phenyl substituted with 1 to 3 groups selected from halogen, nitro, cyano, carboxy, $C_{1-4}$ alkyl, $C_{1-4}$ alkoxy, $C_{1-4}$ alkylthio, halo-suybstituted $C_{1-4}$ alkyl, halo-substituted $C_{1-4}$ alkoxy, halo-substituted $C_{1-4}$ alkylthio and $C_{2-5}$ alkoxycarbonyl, phenoxy, phenoxy substituted with 1 to 3 groups selected from halogen, nitro, cyano, carboxy, $C_{1-4}$ alkyl, $C_{1-4}$ alkoxy, $C_{1-4}$ alkylthio, halo-substituted $C_{1-4}$ alkyl, halo-substituted $C_{1-4}$ alkoxy, halo-substituted $C_{1-4}$ alkylthio and $C_{2-5}$ alkoxycarbonyl, R'R"N— where R' and R" are each hydrogen or $C_{1-4}$ alkyl or R'''CONH— where R''' is $C_{1-4}$ alkyl, $R^6$, $R^7$ and $R^8$ are each $C_{1-6}$ alkyl, halo-substituted $C_{1-6}$ alkyl, phenyl, or phenyl substituted with 1 to 3 groups selected from halogen, nitro, cyano, carboxy, $C_{1-4}$ alkyl, $C_{1-4}$ alkoxy, $C_{1-4}$ alkylthio, halo-substituted $C_{1-4}$ alkyl, halo-substituted $C_{1-4}$ alkoxy, halo-substituted $C_{1-4}$ alkylthio and $C_{2-5}$ alkoxycarbonyl, or $R^6$ and $R^7$, together with the carbon atom to which they are attached, form a cycloalkyl group containing 3 to 7 carbon atoms, or $R^6$, $R^7$ and $R^8$ together with the carbon atom to which they are attached, form a bicycloalkyl group containing 4 to 9 carbon atoms; and salts thereof.

2. A compound according to claim 1 in which $R^3$, $R^4$ and $R^5$ are hydrogen and X is $R^1(HO)C=C(CN)—$ or

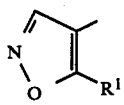

3. A compound according to claim 2 in which X is $R^1$ is $R^1$ is methyl and X is $R^1$

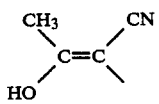

4. A compound of the formula

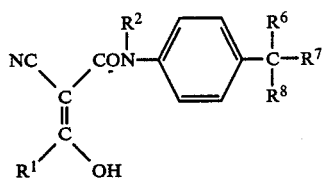

in which $R^1$ is $C_{1-4}$ alkyl, $R^2$ is hydrogen or methyl, and $R^6$, $R^7$ and $R^8$ are each $C_{1-4}$ alkyl; and salts thereof.

5. A compound of the formula

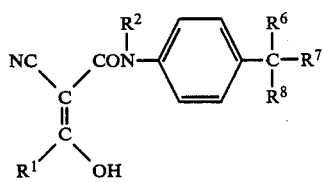

in which $R^1$ is $C_{1-4}$ alkyl, $R^2$ is hydrogen or methyl, $R^6$ and $R^7$ together form a cycloalkyl group of 3 to 7 carbon atoms and $R^8$ is $C_{1-4}$ alkyl; and salts thereof.

6. 2-Cyano-N-[4-(1,1-dimethylethyl)phenyl]-3-hydroxybut-2-enamide.

7. 2-Cyano-N-[4-(1,1-dimethylethyl)phenyl]-3-hydroxy-N-methylbut-2-enamide.

8. A pharmaceutical formulation comprising a compound of the formula

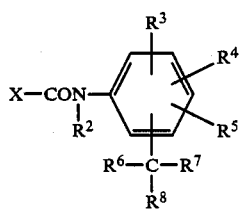

in which X is $R^1(HO)C=C(CN)—$, $R^1(CO)—CH(CN)—$ or

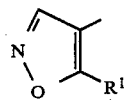

$R^1$ and $R^2$ are each hydrogen or $C_{1-6}$ alkyl, $R^3$, $R^4$ and $R^5$ are each hydrogen, hydroxy, halogen, nitro, cyano, carboxy, $C_{1-4}$ alkyl, $C_{1-4}$ alkoxy, $C_{1-4}$ alkylthio, halo-substituted $C_{1-4}$ alkyl, halo-substituted $C_{1-4}$ alkoxy, halo-substituted $C_{1-4}$ alkylthio, $C_{2-5}$ alkoxycarbonyl, phenyl, phenyl substituted with 1 to 3 groups selected from halogen nitro, cyano, carboxy, $C_{1-4}$ alkyl, $C_{1-4}$ alkoxy, $C_{1-4}$ alkylthio, halo-substituted $C_{1-4}$ alkyl, halo-substituted $C_{1-4}$ alkoxy, halo-substituted $C_{1-4}$ alkylthio and $C_{2-5}$ alkoxycarbonyl, phenoxy, phenoxy substituted with 1 to 3 groups selected from halogen, nitro, cyano, carboxy, $C_{1-4}$ alkyl, $C_{1-4}$ alkoxy, $C_{1-4}$ alkylthio, halo-substituted $C_{1-4}$ alkyl, halo-substituted $C_{1-4}$ alkoxy, halo-substituted $C_{1-4}$ alkylthio and $C_{2-5}$ alkoxycarbonyl, R'R"N— where R' and R" are each hydrogen or $C_{1-4}$ alkyl or R'''CONH— where R''' is $C_{1-4}$ alkyl, $R^6$, $R^7$ and $R^8$ are each $C_{1-6}$ alkyl, halo-substituted $C_{1-6}$ alkyl, phenyl, or phenyl substituted with 1 to 3 groups selected from halogen, nitro, cyano, carboxy, $C_{1-4}$ alkyl, $C_{1-4}$ alkoxy, $C_{1-4}$ alkylthio, halo-substituted $C_{1-4}$ alkyl, halo-substituted $C_{1-4}$ alkoxy, halo-substituted $C_{1-4}$ alkylthio and $C_{2-5}$ alkoxycarbonyl, or $R^6$ and $R^7$, together with the carbon atom to which they are attached, form a cycloalkyl group containing 3 to 7 carbon atoms, or $R^6$, $R^7$ and $R^8$ together with the carbon atom to which they are attached, form a bicycloalkyl group containing 4 to 9 carbon atoms, or a pharmaceutically-acceptable salt thereof, in association with a pharmaceutically-acceptable carrier or diluent therefor.

9. A method of treating an animal, including a human, suffering from or susceptible to a disorder of the immune system or a disease in which leukotrienes are implicated, which comprises administering an effective amount of a compound of the formula

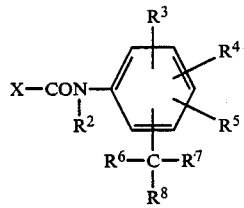

in which X is $R^1(HO)C=C(CN)—$, $R^1(CO)—CH(CN)—$ or

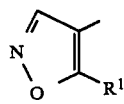

$R^1$ and $R^2$ are each hydrogen or $C_{1-6}$ alkyl, $R^3$, $R^4$ and $R^5$ are each hydrogen, hydroxy, halogen, nitro, cyano, carboxy, $C_{1-4}$ alkyl, $C_{1-4}$ alkoxy, $C_{1-4}$ alkylthio, halo-substituted $C_{1-4}$ alkyl, halo-substituted $C_{1-4}$ alkoxy, halo-substituted $C_{1-4}$ alkylthio, $C_{2-5}$ alkoxycarbonyl, phenyl, phenyl substituted with 1 to 3 groups selected from halogen, nitro, cyano, carboxy, $C_{1-4}$ alkyl, $C_{1-4}$ alkoxy, $C_{1-4}$ alkylthio, halo-substituted $C_{1-4}$ alkyl, halo-substituted $C_{1-4}$ alkoxy, halo-substituted $C_{1-4}$ alkylthio and $C_{2-5}$ alkoxycarbonyl, phenoxy, phenoxy substituted with 1 to 3 groups selected from halogen, nitro, cyano, carboxy, $C_{1-4}$ alkyl, $C_{1-4}$ alkoxy, $C_{1-4}$ alkylthio, halo-substituted $C_{1-4}$ alkyl, halo-substituted $C_{1-4}$ alkoxy, halo-substituted $C_{1-4}$ alkylthio and $C_{2-5}$ alkoxycarbonyl, R'R''N— where R' and R'' are each hydrogen or $C_{1-4}$ alkyl or R'''CONH— where R''' is $C_{1-4}$ alkyl, $R^6$, $R^7$ and $R^8$ are each $C_{1-6}$ alkyl, halo-substituted $C_{1-6}$ alkyl, phenyl, or phenyl substituted with 1 to 3 groups selected from halogen, nitro, cyano, carboxy, $C_{1-4}$ alkyl, $C_{1-4}$ alkoxy, $C_{1-4}$ alkylthio, halo-substituted $C_{1-4}$ alkyl, halo-substituted $C_{1-4}$ alkoxy, halo-substituted $C_{1-4}$ alkylthio and $C_{2-5}$ alkoxycarbonyl, or $R^6$ and $R^7$, together with the carbon atom to which they are attached, form a cycloalkyl group containing 3 to 7 carbon atoms, or $R^6$, $R^7$ and $R^8$ together with the carbon atom to which they are attached, form a bicycloalkyl group containing 4 to 9 carbon atoms, or a pharmaceutically-acceptable salt thereof.

* * * * *

UNITED STATES PATENT AND TRADEMARK OFFICE
CERTIFICATE OF CORRECTION

PATENT NO. : 4,892,963

DATED : January 9, 1990

INVENTOR(S) : Peter T. Gallagher et al.

It is certified that error appears in the above-identified patent and that said Letters Patent is hereby corrected as shown below:

Column 2, line 35, add a bond between the $R^2$ group and the nitrogen atom of the CON group.

Column 8, line 25, add a bond between the $R^2$ group and the nitrogen atom of the CON group.

Column 15, line 18, delete "$R^1$ is $R^1$ is methyl and X is $R^1$".

Column 16, line 14, insert a comma after "halogen".

Signed and Sealed this

Twelfth Day of March, 1991

Attest:

HARRY F. MANBECK, JR.

Attesting Officer

Commissioner of Patents and Trademarks